United States Patent
Park et al.

(10) Patent No.: US 9,848,834 B2
(45) Date of Patent: Dec. 26, 2017

(54) METHOD FOR DETECTING POSITIONS OF TISSUES AND APPARATUS USING THE SAME

(71) Applicant: CUREXO, Inc, Seoul (KR)

(72) Inventors: Young-bae Park, Cheongju-si (KR); Chang-hun Song, Goyang-si (KR); Jae-jun Lee, Suwon-si (KR)

(73) Assignee: CUREXO, INC, Seoul (KR)

( * ) Notice: Subject to any disclaimer, the term of this patent is extended or adjusted under 35 U.S.C. 154(b) by 294 days.

(21) Appl. No.: 14/712,090

(22) Filed: May 14, 2015

(65) Prior Publication Data
US 2015/0332458 A1    Nov. 19, 2015

(30) Foreign Application Priority Data

May 16, 2014  (KR) .................. 10-2014-0059238

(51) Int. Cl.
*A61B 6/00* (2006.01)
*A61B 6/03* (2006.01)
(Continued)

(52) U.S. Cl.
CPC ............... *A61B 6/03* (2013.01); *A61B 6/032* (2013.01); *A61B 19/2203* (2013.01);
(Continued)

(58) Field of Classification Search
CPC .......... A61B 6/03; A61B 90/00; A61B 6/032; A61B 19/2203; A61B 19/56; A61B 34/30;
(Continued)

(56) References Cited

U.S. PATENT DOCUMENTS 5,234,432 A * 8/1993 Brown .................. A61B 17/15
606/79
5,480,400 A * 1/1996 Berger ............... A61B 17/7225
604/96.01
(Continued)

OTHER PUBLICATIONS

Ballantyne et al., 2004, "Primer of Robotic & Telerobotic Surgery". pp. 1-7.*
(Continued)

*Primary Examiner* — Manav Seth
(74) *Attorney, Agent, or Firm* — Kile Park Reed & Houtteman PLLC

(57) ABSTRACT

Disclosed is a method for detecting positions of body tissues and an apparatus using the method. The apparatus according to the present invention comprises a surgery information storage unit storing an examined first image associated with a target bone of surgery, a position measuring unit measuring position values of multiple points on a surface of the target bone of surgery before and after cutting, and a registration control unit for acquiring a second image regarding the remained bone after cutting by applying the shape of the bone changed according to the progression of bone cutting to the first image, and for performing position registration with respect to the second image by using the position values of multiple points on surface of the target bone of surgery after cutting, which is measured by the position measuring unit.

6 Claims, 7 Drawing Sheets

(51) Int. Cl.
  *G06T 7/00*     (2017.01)
  *A61B 19/00*    (2006.01)
  *G06T 1/00*     (2006.01)
  *G06T 15/08*    (2011.01)
  *A61B 90/00*    (2016.01)
  *G06T 7/73*     (2017.01)
  *A61B 34/30*    (2016.01)

(52) U.S. Cl.
  CPC .............. *A61B 19/56* (2013.01); *A61B 90/00* (2016.02); *G06T 1/0007* (2013.01); *G06T 7/0016* (2013.01); *G06T 7/75* (2017.01); *G06T 15/08* (2013.01); *A61B 6/505* (2013.01); *A61B 34/30* (2016.02); *G06T 2207/10016* (2013.01); *G06T 2207/10028* (2013.01); *G06T 2207/10081* (2013.01); *G06T 2207/20221* (2013.01); *G06T 2207/30008* (2013.01); *G06T 2207/30052* (2013.01); *G06T 2207/30096* (2013.01)

(58) Field of Classification Search
  CPC ......... A61B 6/505; G06T 7/75; G06T 1/0007; G06T 7/0016; G06T 15/08; G06T 2207/10016; G06T 2207/10028; G06T 2207/10081; G06T 2207/20221; G06T 2207/30008; G06T 2207/30052; G06T 2207/30096
  See application file for complete search history.

(56) References Cited

U.S. PATENT DOCUMENTS

| | | | | |
|---|---|---|---|---|
| 5,682,886 A * | 11/1997 | Delp | ................... | A61B 17/154 128/920 |
| 5,824,085 A * | 10/1998 | Sahay | ...................... | A61F 2/46 128/898 |
| 6,033,415 A * | 3/2000 | Mittelstadt | ............ | G06T 3/0006 128/922 |
| 8,160,345 B2 * | 4/2012 | Pavlovskaia | .............. | G06T 7/13 382/131 |
| 8,597,362 B2 * | 12/2013 | Shenoy | .................. | A61B 17/56 623/20.21 |
| 8,617,171 B2 * | 12/2013 | Park | ...................... | G06T 7/0012 606/87 |
| 8,617,175 B2 * | 12/2013 | Park | .................... | A61B 17/155 606/89 |
| 8,632,552 B2 * | 1/2014 | Bonutti | ................ | A61B 17/025 606/130 |
| 8,634,629 B2 * | 1/2014 | Wilson | .................. | A61B 6/466 382/132 |
| 8,715,291 B2 * | 5/2014 | Park | ...................... | A61B 17/15 606/87 |
| 8,737,700 B2 * | 5/2014 | Park | ....................... | A61B 5/055 382/128 |
| 8,801,719 B2 * | 8/2014 | Park | ..................... | A61B 17/154 606/86 R |
| 8,936,596 B2 * | 1/2015 | Mittelstadt | ............ | A61B 17/17 606/79 |
| 8,953,856 B2 * | 2/2015 | Ostrovsky-Berman | ................ | G06T 7/0032 382/128 |
| 9,017,336 B2 * | 4/2015 | Park | .................... | A61B 17/155 606/88 |
| 9,101,397 B2 * | 8/2015 | Guthart | .............. | A61B 19/5244 |
| 9,402,726 B2 * | 8/2016 | Linderman | .......... | A61B 17/155 |
| 2003/0208296 A1 * | 11/2003 | Brisson | .................. | A61B 90/10 700/117 |
| 2006/0155293 A1 * | 7/2006 | McGinley | ............ | A61B 17/155 606/87 |
| 2008/0074422 A1 * | 3/2008 | Dekel | ..................... | G06T 15/08 345/427 |
| 2009/0190815 A1 * | 7/2009 | Dam | .................... | A61B 5/055 382/131 |
| 2010/0310141 A1 * | 12/2010 | Wilson | ................... | A61B 6/466 382/131 |
| 2014/0093153 A1 * | 4/2014 | Sofka | .................... | G06T 7/0014 382/131 |
| 2015/0305828 A1 * | 10/2015 | Park | ........................ | G09G 5/14 345/629 |
| 2015/0342462 A1 * | 12/2015 | Park | ..................... | A61B 5/0071 600/431 |
| 2016/0125603 A1 * | 5/2016 | Tanji | ..................... | A61B 17/152 382/131 |

OTHER PUBLICATIONS

Herline et al., 2000, "Surface registration for use in interactive, image guided liver surgery". pp. 1-7.*

* cited by examiner (a)

(b)

(c)

METHOD FOR DETECTING POSITIONS OF TISSUES AND APPARATUS USING THE SAME

BACKGROUND OF THE INVENTION

1. Field of the Invention

The present invention relates to detection of positions of tissues. More specifically, the present invention relates to a method for detecting positions of body tissues and an apparatus using the method.

2. Description of the Related Art

The deepening of a low birthrate and an aging phenomenon is acting as a catalyst in developing robotic industry. As the need for smart robots working instead of people increases, the worldwide robot market is rapidly expanding. The robots can be utilized in various fields, including operations in biologically dangerous regions like the scene of a fire, the reconnaissance in battlefield, and the lengthy surgery.

Among those robots, medical robots have been being developed focusing most on user convenience. The main principles in developing medical robots are to provide convenience in using to doctors, to provide no inconvenience to patients, to minimize invasions of patients, to minimize pains of patients, etc. The medical robot technology is a technic field combining BT (Bio-Tech), NT (Nano-Tech), RT (Robot-Tech), and MT (Medical-Tech).

The orthopedic surgery using a robot enables precise bone cutting. For this, there is a need to figure out positions of bones before surgery. It also needs to be figured out that whether the positions of bones have been changed during surgery, and how much the bones have been moved, if it has been changed.

During surgery, as methods for figuring out the positions of bones, there are method using anatomical shapes, method using the center of joints, method that matches a shape of bone that is obtained from medical images with a shape of bone exposed in surgery, etc.

However, after a step of bone cutting using a robot has started, when trying to figure out the positions of bones again before the step of bone cutting is finished, there is a problem that such methods cannot be used because the bone was amputated already.

After the bones has been moved, in order to figure out the positions of bones again, the existing surgery robots use a method that attaches extra markers (for example, screws or nails) to bones, and figures out the positions of bones again based on the positions of markers. Although such method is neat and quick, it causes damage to bones due to screws or nails that are inserted into bones.

Furthermore, because positions where markers can be attached without disturbing the surgery are limited, a recent minimally invasive surgery has problems that the amount of incision is increased in order to attach markers, and that the markers have to be attached through tissues.

SUMMARY OF THE INVENTION

An object of the present invention, which is to overcome aforementioned problems, is to provide a method for detecting positions of tissues, which detects of the positions of bones using cut surfaces.

Another object of the present invention is to provide an apparatus using the method for detecting positions of tissues.

In accordance with one aspect of the present invention, there is provided an apparatus for detecting positions of tissues including a surgery information storage unit storing an examined first image associated with a target bone of surgery, a position measuring unit measuring position values of multiple points on a surface of the target bone of surgery before and after cutting, and a registration control unit for acquiring a second image regarding the remained bone after cutting by applying the shape of the bone changed according to the progression of bone cutting to the first image, and for performing position registration with respect to the second image by using the position values of multiple points on surface of the target bone of surgery after cutting, which is measured by the position measuring unit.

The shape of the remained bone after cutting could include a unique shape used in performing the position registration, and the unique shape could include staircase shapes, groove shapes, and fluted shapes.

The registration control unit could perform a first position registration by calculating a first transformation matrix between the first image defined on a first coordinate system and the first image defined on a second coordinate system. The first coordinate system is a coordinate system on which an image of the target bone of surgery that is examined in advance before surgery is defined, and the second coordinate system is a coordinate system regarding the bone existing in surgery room.

The registration control unit could perform a second position registration by calculating a second transformation matrix between the second image defined on the first coordinate system and the second image defined on the second coordinate system.

A difference between the first transformation matrix and the second transformation matrix could mean the quantity of movement of the bone.

The registration control unit could derive the second image defined on the first coordinate system by using the first transformation matrix.

The apparatus for detecting positions of tissues could further include a display unit displaying the second image that is changed according to the progression of bone cutting.

In accordance with another aspect of the present invention, there is provided a method for detecting positions of tissues including acquiring a first image associated with a target bone of surgery in a first coordinate system prior to surgery, measuring position values of multiple points on a surface of the target bone of surgery in a second coordinate system, and performing a first position registration between the first coordinate system and the second coordinate system with respect to the first image, acquiring a second image regarding the remained bone after cutting in the second coordinate system by applying the shape of the bone changed according to the progression of bone cutting to the first image, acquiring the second image in the first coordinate system by using a level of the progression of bone cutting, and performing a second position registration with the second image defined on the first coordinate system and the second image defined on the second coordinate system.

The step of performing the first position registration between the first coordinate system and the second coordinate system with respect to the first image could comprise performing the first position registration by calculating a first transformation matrix between the first image defined on the first coordinate system and the first image defined on the second coordinate system.

In addition, the step of performing the second position registration with the second image defined on the first coordinate system and the second image defined on the second coordinate system could comprise performing the second position registration by calculating a second transformation matrix between the second image defined on the first coordinate system and the second image defined on the second coordinate system.

The step of acquiring the second image in the first coordinate system by using the level of the progression of bone cutting could comprise deriving the second image defined on the first coordinate system by using the first transformation matrix.

The step of acquiring the second image in the first coordinate system by using the level of the progression of bone cutting could comprise calculating a volume of the second image by subtracting a transformed volume of bone from a defined volume of bone. The transformed volume of bone is a volume of cut bone that has been transformed into the first coordinate system, and the defined volume is a volume defined by information of the first image on the first coordinate system.

In a situation that the bone cutting is done using a surgical robot controlled by a computer, in order to re-search or re-check the positions of bones being cut, the method and the apparatus use shapes of bones being cut which are calculated according to the present invention. Therefore, it is possible to avoid damages of tissues or extra surgeries caused by attaching extra markers to bones, and protect bones and tissues of a patient.

In addition, according to the present invention, the method and the apparatus can save processing time for position registration by using the shapes of bones cut into unique shapes.

DETAILED DESCRIPTION OF THE INVENTION

Figure 1:
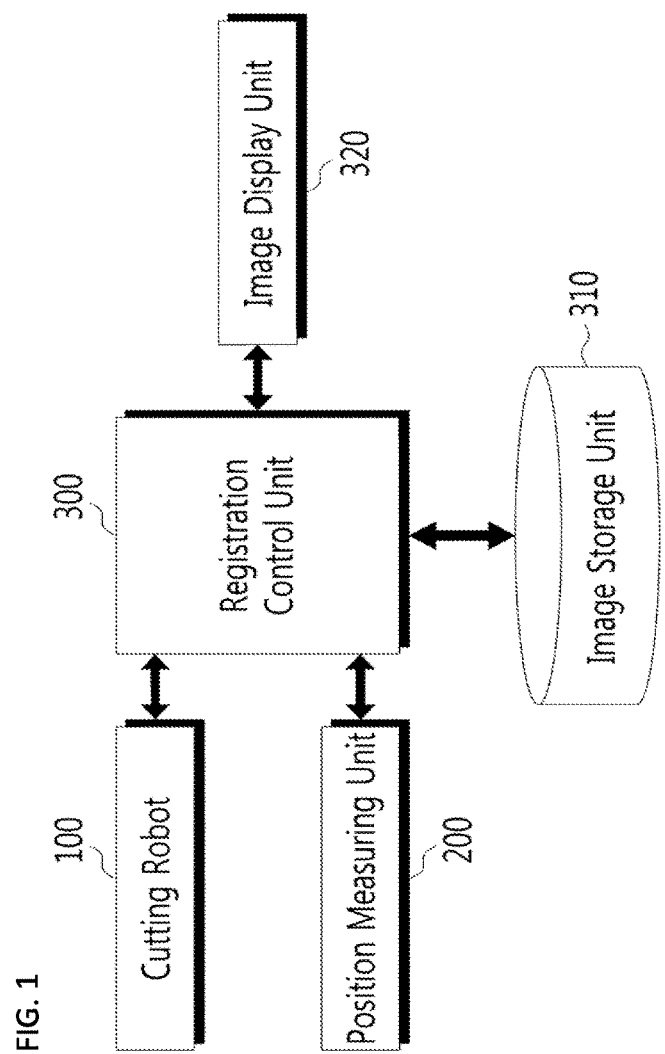
FIG. 1 is a schematic diagram of an apparatus for detecting positions of tissues according to the present invention.

Hereinafter, exemplary embodiments of the present invention will be described in detail. However, the present invention is not limited to the exemplary embodiments disclosed below, but can be implemented in various forms. The following exemplary embodiments are described in order to enable those of ordinary skill in the art to embody and practice the invention.

It will be understood that, although the terms first, second, etc. may be used herein to describe various elements, these elements should not be limited by these terms. These terms are only used to distinguish one element from another. For example, a first element could be termed as a second element, and similarly, a second element could be termed as a first element, without departing from the scope of the present invention. The term and/or used herein includes any or all combinations of one or more of the associated listed items.

It will be understood that when an element is referred to as being connected or coupled to another element, it can be directly connected or coupled to the other element or intervening elements may be present.

The terminology used herein is for the purpose of describing particular embodiments only and is not intended to be limiting of the invention. As used herein, the singular forms a, an and the are intended to include the plural forms as well, unless the context clearly indicates otherwise. It will be further understood that the terms comprises, comprising, includes and/or including, when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meanings as commonly understood by one of ordinary skill in the art to which this invention belongs. It will be further understood that terms, such as those defined in commonly uses dictionaries, should be interpreted as having a meaning that is consistent with their meaning in the context of the relevant art and will not be interpreted in an idealized or overly formal sense unless expressly so defined here.

Hereinafter, preferred embodiments of the present invention will be described in detail with the accompanying drawings. In the following description, the same reference numerals denote the same elements to facilitate the overall understanding, and repeated description thereof will be omitted.

FIG. 1 is a schematic diagram of an apparatus for detecting positions of tissues according to the present invention.

Hereafter, the elements according to the present invention, which will be described by referring to FIG. 1, are those elements defined by functional classification not by physical classification. The elements according to the present invention could be defined by functions performed by each of the elements. Each of the elements could be implemented as hardware and/or program codes performing each function and processing units. They also could be implemented so that the functions of two or more elements are included in one element. Therefore, it needs to be noted that the names of elements, given in following embodiments, are not for distinguishing elements physically, for representing main function performed by each element. Furthermore, it needs to be noted that the spirit of the present invention is not be limited by the names of elements.

As illustrated in FIG. 1, the apparatus for detecting positions of tissues according to the present invention comprises a cutting robot 100 to which surgery equipment for cutting bones using an orthopedic surgery robot is attached, a position measuring unit 200 measuring positions of bones, a registration control unit 300, an image storage unit 310, and an image display unit 320.

The position measuring unit 200 measures the position of a bone exposed outwards by incising skins and skin tissues in surgery. Digitizers, infrared units, laser units, etc. could be used for measuring the position of a bone. The position measuring unit 200 measures not only the position of a bone before cutting but also the positions of many points including a cut surface after cutting.

The registration control unit 300 determines the real position of a bone by matching three-dimensional shape images of the bone, which is obtained before surgery by computerized tomography equipment, etc., with three-dimensional position data obtained by the position measuring unit 200. Therefore, the cutting robot 100 can determine exact cutting positions, and cutting paths.

Herein, the step of matching the three-dimensional shape images of the bone, which is obtained before surgery by computerized tomography equipment, etc., with the three-dimensional position data obtained by the position measuring unit 200 is referred to as registration. In robotic surgery, the position registration is a step to calculate preferred surgery positions based on the anatomical position of bones measured by an anatomical position finder and a surgery robot.

Although, there are various methods for registration, the most representative registration method will be explained hereafter.

In robotic surgery, the coordinate systems are classified into a first coordinate system defined with respect to images of a target bone of surgery, which is obtained beforehand, and a second coordinate system about a bone of a patient in real surgery. For registration, calculate a transformation matrix T between the first coordinate system and the second coordinate system, and apply the transformation matrix T into the first coordinate system. Thus, a processing path of robot can be applied appropriately according to the real position of the bone.

As the registration methods for calculating the transformation matrix T, there are pin-basis registration, image-basis registration, etc.

According to the pin-basis registration method, before surgery, multiple pins are inserted into the bone. Then, CT images are taken, with the pins inserted from a lesion above a bone of a patient. After that, the processing path of robot is determined based on the CT images. In this case, a reference coordinate system of the processing path of robot is established by the pins on the CT images.

As completed the set-up of the processing path of robot, the registration is performed by matching the real pins inserted into the surgical region with the pins on the CT images that are basis of the processing path of robot. Such pin-basis registration method causes pain and discomfort of patients due to multiple pins inserted into a lesion from start to the end of the surgery.

According to the image-basis registration method, meanwhile, the processing path of robot is determined based on CT images of a thighbone of a patient that are obtained before surgery. In the early days, the registration was made by matching three-dimensional images obtained from CT images with two-dimensional X-ray images of bones of patients obtained in real surgery. Such method causes many errors in the process of distinguishing tissues like bone tissues, ligaments, etc. and in the process of detecting edges.

To reduce such errors, recently, the registration method that matches a particular point of a pre-surgery CT image with a particular point measured by digitizer during surgery has been being used. According to the registration method using the digitizer, the registration is performed by measuring the particular point of bone tissues with a measuring pin of digitizer in surgery.

The three-dimensional shape images of bones, which are obtained before surgery by computerized tomography equipment, etc., are stored in the image storage unit 310.

Furthermore, the registration control unit 300 calculates cut shapes and cut quantity of bones in real time according to cutting operations performed by the cutting robot 100. When needing re-registration due to movements of tissues etc., the registration control unit 300 calculates new transformation matrix by using the calculated cut shapes and cut quantity, and performs re-registration.

Meanwhile, the image display unit 320 displays images regarding bone tissues changed by cutting in the process of the surgery, based on the cut shapes and the cut quantity calculated by the registration control unit 300.

The present invention suggests a method that calculates a cut surface and a cut volume of a bone that has been processed by the robot, and re-finds the position of the bone by using the cut surface.

According to the present invention, when trying to reconfirm the position of the bone during surgery, it measures surfaces of the bone including the cut surface and calculates the position of the bone that can integrate the measured surfaces and the image data.

According to the present invention, when the robot cuts bones, it generates geometric shapes (staircase shape, groove shape, fluted shape) intentionally. When trying to measure the cut surface, the cut surface can be measured more easily and simply by using such geometric shapes. However, the geometric shapes, which are not need in surgery, should be generated on parts of the bone that will be removed or cut off in final cut step, so that they do not influence the result of surgery.

Figure 2:
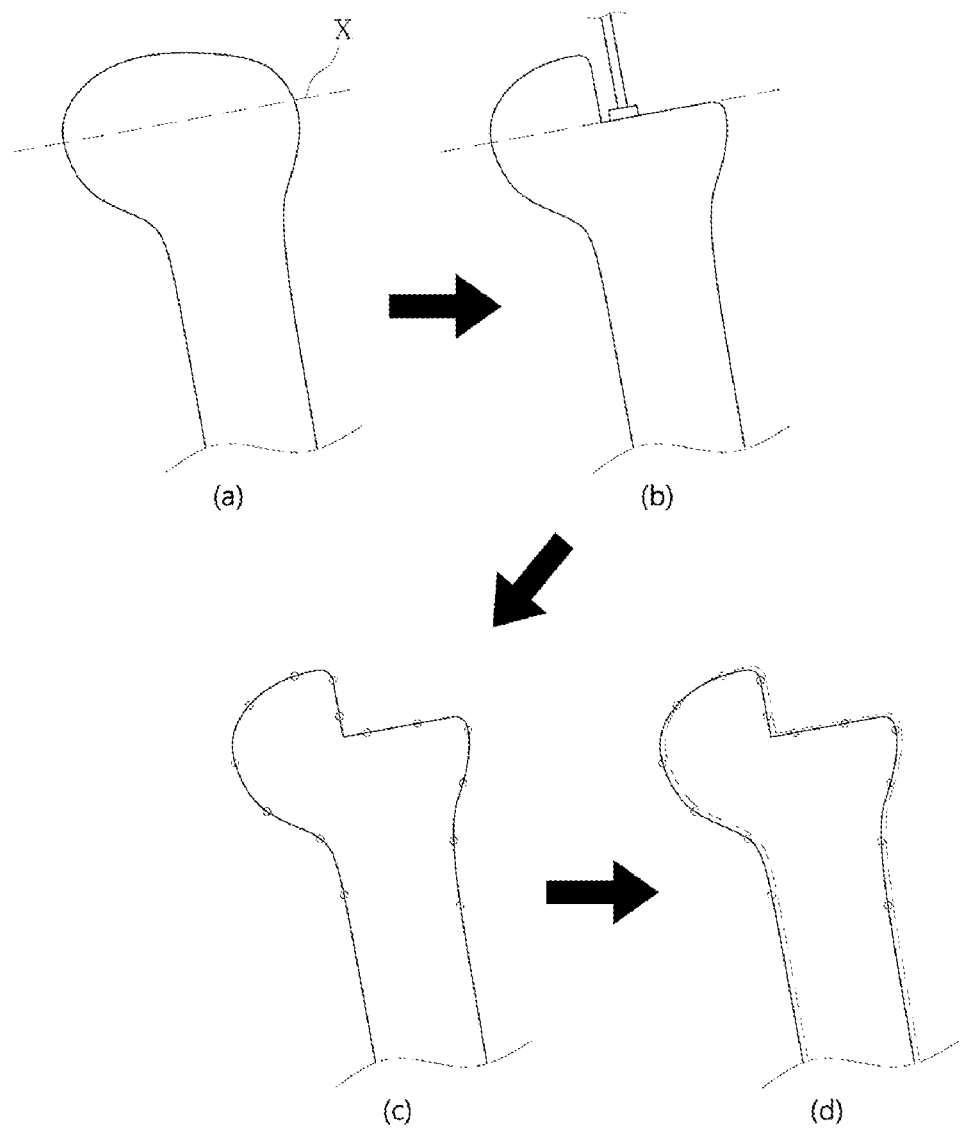
FIG. 2 notionally illustrates an example of a method for detecting positions of tissues according to the present invention.

FIG. 2 notionally illustrates an example of a method for detecting positions of tissues according to the present invention.

In other words, FIG. 2 illustrates a concept for cutting bones into particular shapes during surgery and detecting movements of positions of bones by using them and a procedure thereof.

As illustrated in FIG. 2, when trying to cut a bone flatwise in X direction like shown in a of FIG. 2, the bone is cut into a staircase shape before the robot finishes cutting operations as shown in b of FIG. 2, and the position measuring unit 200 measures surfaces of the bone including the cut surface as shown in c of FIG. 2. Consequently, the position of the bone can be re-measured by comparing those measured points with a model including the original shape of the bone, which is stored in a computer, and the cut shape as shown in d of FIG. 2.

Figure 3:
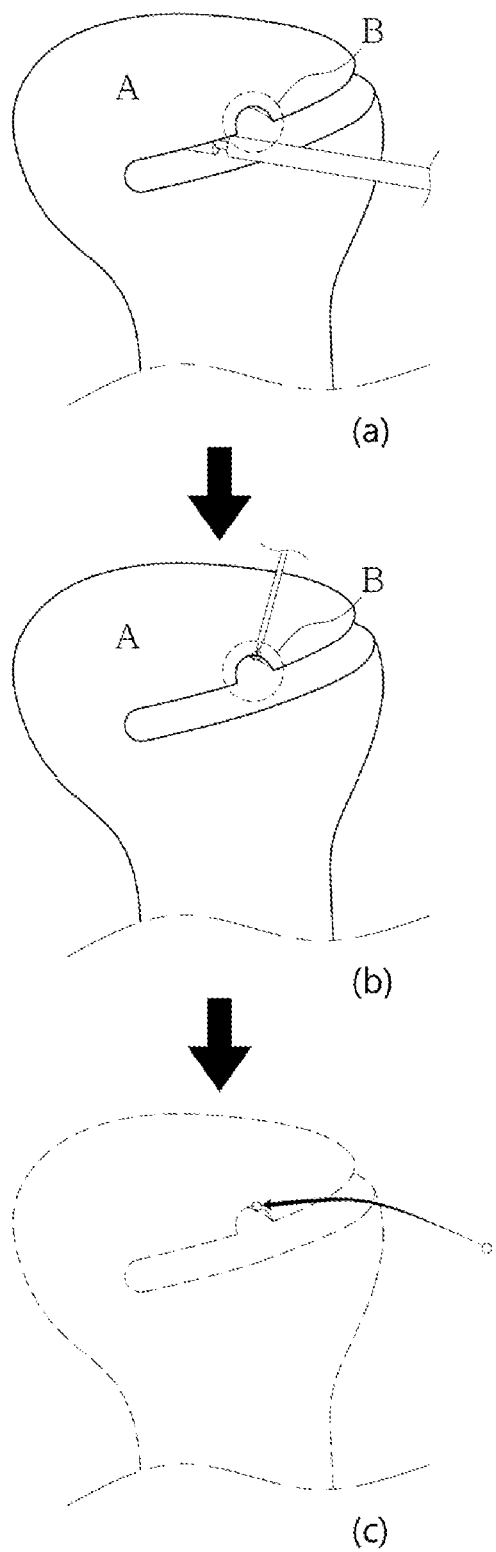
FIG. 3 notionally illustrates another example of the method for detecting positions of tissues according to the present invention.

FIG. 3 notionally illustrates another example of the method for detecting positions of tissues according to the present invention.

In a shape of bone illustrated in FIG. 3, an upper part of bone A is a part to be removed. According to the present invention, during cutting operations, the cutting robot 100 generates a particular shape, for example, a groove B, etc. on the upper part of bone A. After that, when trying to measure a surface of bone due to necessity of the re-registration of bone, it measures corners generated by the groove B. Then it calculates assuming that the groove B is a corresponding corner part of the original shape of bone stored in the image storage unit 310; thereby reducing calculating time for the re-registration and errors.

That is, the embodiment of FIG. 3 shows that calculating time for the registration and errors can be reduced by cutting a bone so that the cut shape includes particular patterns or curves and by measuring the patterns or curves. FIG. 3 also shows that the targeted shape of bone has no influence by generating the particular shape added for these objectives (corner B in FIG. 3) on area of the bone that is to be removed.

By generating the particular shape and measuring the particular shape, errors and calculating time can be reduced in calculation for the registration. In general, for position registration, algorithms that find positions where multiple points are matched as much as possible with a particular shape are commonly used (least square method is generally used). According to these algorithms, the errors tend to reduce if the shape has curves or peaks. Moreover, the reason the calculating time is reduced is that the calculating time can be reduced, when knowing roughly that the measured points are in which part.

In other words, the embodiment of FIG. 3 makes the registration easier by marking on the part of bone tissues that are to be finally cut away. Thus, the embodiment of FIG. 3 is one of the methods to increase efficiency of calculating for the registration and reduce errors.

Hereafter, with referring FIG. 4 to FIG. 6, the method of registration using pre-processed positions of the present invention will be explained in detail.

In order to match a known position of bone on the coordinate system of CT with a position of bone on the coordinate system of robot in real space, a transformation matrix between the two coordinates should be calculated. Firstly, suppose S denotes an original surface of bone and $V_n$ (for n points) denotes a position on the surface of bone. Calculate the transformation matrix T that minimizes sum of the shortest distance between each point on the surface of bone and surface S. Moreover, considering the cut shape, update S into S' and calculate new transformation matrix by recalculating with respect to new position $V_n'$.

Further detailed explanations are as follows.

Figure 4:
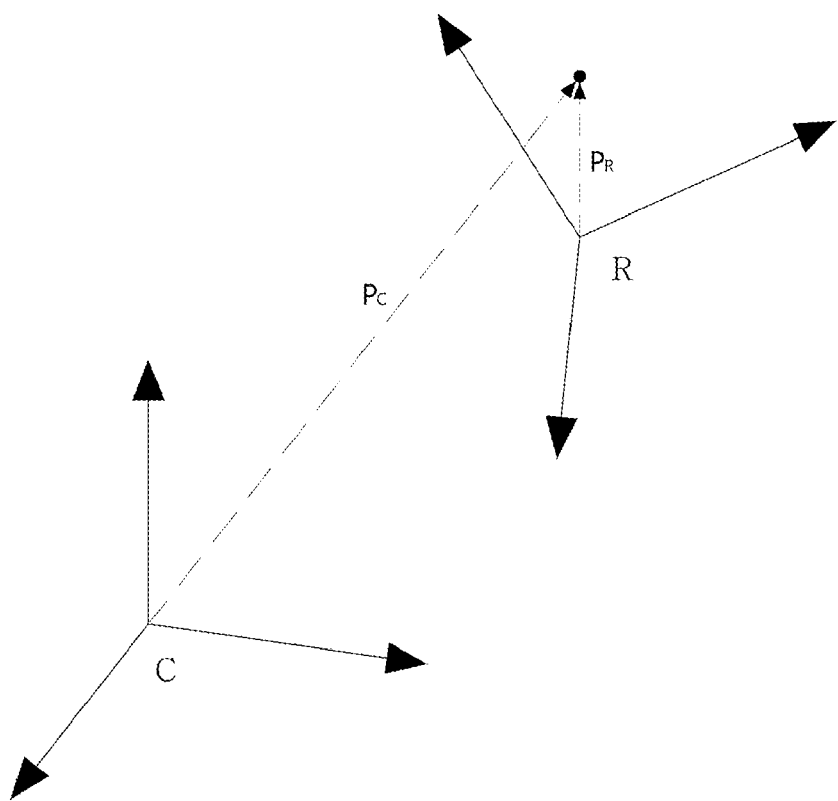
FIG. 4 is a conceptual diagram of registration according to the present invention.

FIG. 4 is a conceptual diagram of a registration according to the present invention.

In FIG. 4, C denotes the coordinate system of CT having pre-obtained images of bone by using CT, and R denotes the coordinate system of robot in real space, surgery room. The goal of the registration is to calculate the transformation matrix between the two coordinate systems. When $P_C$ denotes one point on the coordinate system C, $P_C$ can be represented as a point on the coordinate system R as the following equation.

$$P_R = T_C^R \cdot P_C \qquad \text{<Equation 1>}$$

Herein, $T_C^R$ represents a transformation matrix that defines a transformation from the coordinate system C into the coordinate system R.

Secondly, suppose S(P) denotes the shortest distance from one point P to surface S. In this case, if the P exists on the surface S, the S(P) is zero, S(P)=0, if not, the S(P) is zero or bigger than zero, S(P)≥0. That is, the spatial surface is defined by the equation S(P)=0, and the surface defined on the coordinate system C is expressed as $S_C(P_C)$.

Besides, a volume, which is a space surrounded by the S(P), is defined as V(P) and the V(P) is bigger than zero, (P)≥0, In case of a curved surface, because S(P) is the shortest distance to the surface, S(P) is always a positive value. In case of a volume, on the other hand, the sign of the volume is changed according to whether the volume is on the inside or outside of the space.

In addition, if the arithmetic operations between two volumes ($V_1, V_2$), such as subtraction, addition, etc. are allowed, the subtraction of $V_2$ from $V_1$ could represented as $V_1 - V_2 = V_1 \cap (\sim V_2)$, and the addition of $V_1$ and $V_2$ could represented as $V_1 + V_2 = V_1 \cup V_2$.

For calculating of real volume, a method that calculates numerically with dividing the space into raster formats could be used. Furthermore, as another method for calculating of real volume, there is a method that extracts a boundary surface from two volumes and after calculating the boundary surface, makes new corresponding boundary surface and then makes a volume based on the new corresponding boundary surface. According to the method that calculates numerically with dividing the space into raster formats, although it has advantages that the calculation is simple and stable, it needs a lot of calculation time and storage area in order to obtain accuracy in the calculation.

Hereafter, a method that calculates a cut volume of a cutting tool used in robotic surgery will be explained.

Figure 5:
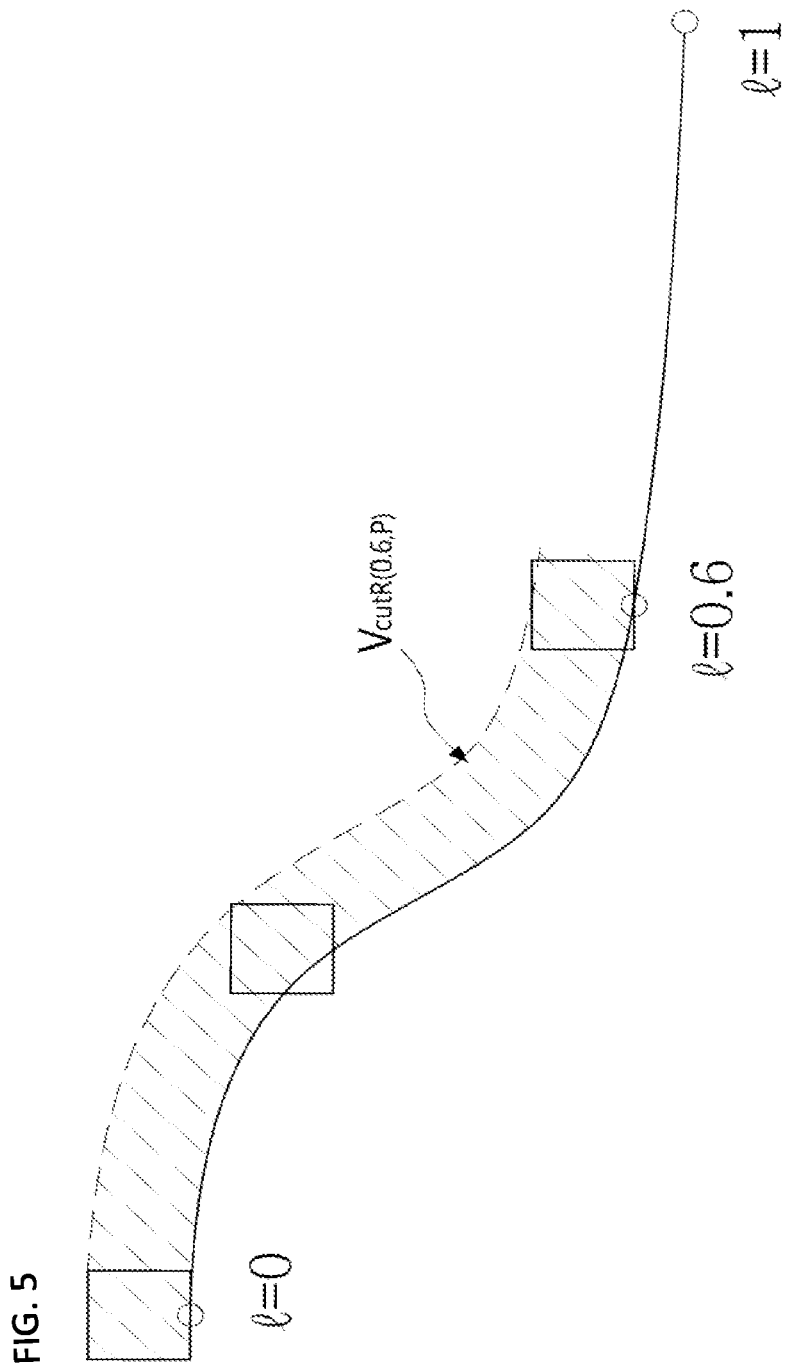
FIG. 5 is a conceptual diagram of a method for calculating a cut volume according to the present invention.

FIG. 5 is a conceptual diagram of a method for calculating a cut volume according to the present invention.

Suppose that the cutting tool exists in a space, and there is a cutting path planned so that the cutting tool can pass through. The progression of the cutting path could be represented as a variable 1. According to the progression of the cutting path, a cut volume is determined. Therefore, adding up all volumes that the cutting tool has passed through according to the progression of the cutting path, the cut volume $V_{cut}$ can be then calculated as the following equation 2.

$$V_{cut\ R}(I,P) = \int_0^l V_{tool\ R}(I) dl \qquad \text{<Equation 2>}$$

In equation 2, the cutting path and the cut volume are defined on the robot coordinate system R, l represents the cutting path, and $V_{tool\ R}(l,P)$ represents the volume on given value of the cutting path l.

Thus, in a CT image, a volume of a bone that is being processed on the coordinate system C can be obtained by subtracting a cut volume, which has been cut so far and is converted into the coordinate system C, from a volume of bone defined in image information of original bones stored in the coordinate system C. This can be expressed as the following equation 3.

$$V_{Bone\ C}(I,P) = V_{Bone\ C}(0) \cup \sim (T_R^C \int_0^l V_{tool\ R}(I) dl) \qquad \text{<Equation 3>}$$

Herein, $V_{Bone\ C}(I,P)$ represents the volume of bone being processed in the CT image, and $T_R^C$ represents a transformation matrix showing the relationship between the coordinate system R and the coordinate system C. $V_{Bone\ C}(0)$ represents the volume of the original bone stored in the coordinate system C.

After that, according to a first registration before processing, measure multiple points of surface of the bone, and calculate a transformation matrix that minimizes a distance between coordinates $P_{Ri}$ of the measured points and the surface of the bone that is on the coordinate system C. In other words, the registration can be defined as a process to calculate the transformation matrix $T_R^C$ that minimizes the distance between the coordinates of the real measured points on the coordinate system of bone R and the surface of the bone that is on the coordinate system C. The registration can be expressed as the following equation 4.

$$\phi(T_R^C) = \sum_{i=0}^n |V_{Bone\ C}(0, T_R^C P_{Ri})| \qquad \text{<Equation 4>}$$

Herein, $\phi(T_R^C)$ represents the distance between the coordinates of the measured points and the surface of bone that is on the coordinate system C, $T_R^C$ represents the transformation matrix showing the relationship between the coordinate system R and the coordinate system C, and $P_{Ri}$ represents the measured point on the coordinate system R.

When an objective function is defined, a problem that finds a variable minimizing the objective function is called as an optimization problem. For solving the optimization problem, an analytic method or a numerical method can be used. In addition, in equation 4, although the objective function was defined simply as the numerical sum of errors, as another example, the objective function can be defined as a sum of squares of errors or a norm of errors, and so on. Accordingly, the efficiency and accuracy of the numerical calculation can be increased.

Figure 6:
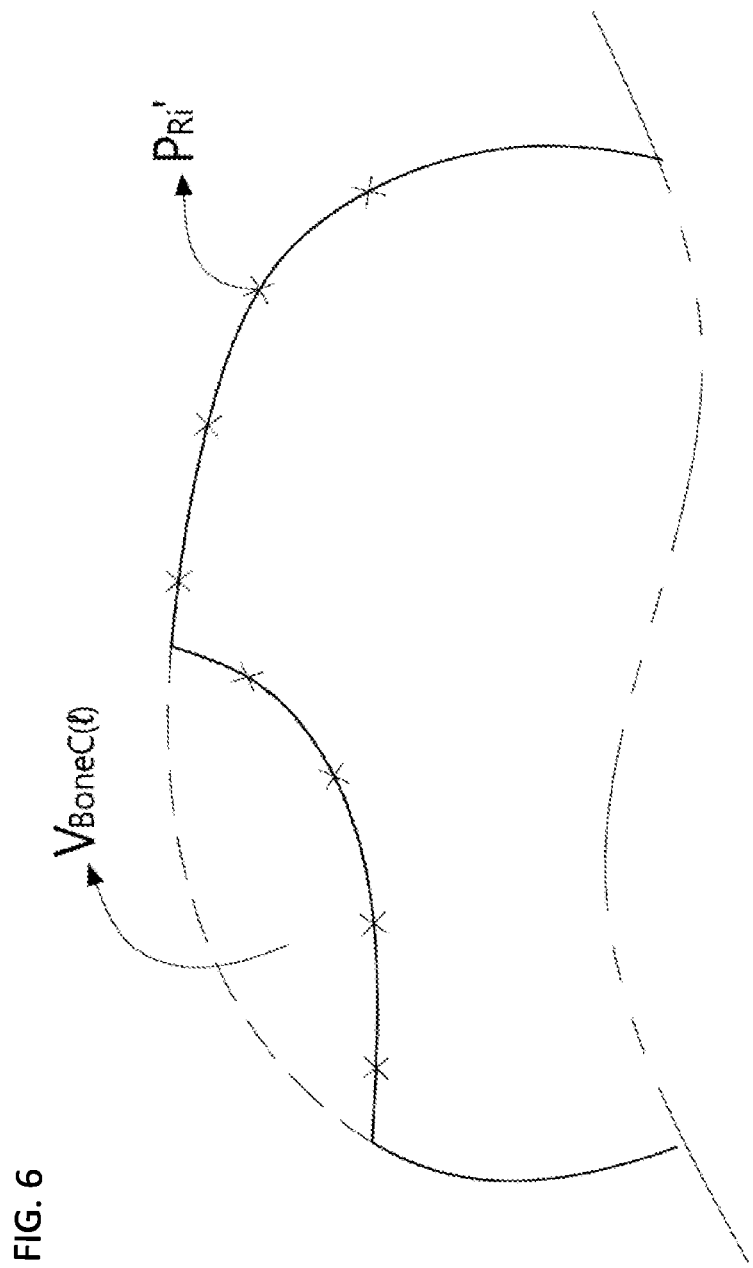
FIG. 6 illustrates a concept of the cut volume defined by cut distance according to the present invention.

FIG. 6 illustrates a concept of the cut volume defined by cut distance according to the present invention.

As illustrated in FIG. 6, $P'_{Ri}$ represents a position of new measured point on the coordinate system R, including a cut surface. $P'_{Ri}$ includes a point on the surface of the original bone, and a point on the cut surface. The volume of cut bone is expressed as $V_{Bone\_C}$ (l), and can be defined as a function of the distance that the cutting robot has moved for cutting.

In this regard, for some reason, when a re-registration, that is, a second registration is performed after the first registration, new transformation matrix $T_R^{C'}$ can be calculated using the same method, based on the bone shape $V_{Bone\_C}$ so far calculated using the transformation matrix $T_R^C$ which have been calculated already and the position of new measured point on the coordinate system R including the cut surface.

That is, in case that the bone has been moved for some reason, the equation for calculating the new transformation matrix $T_R^{C'}$ can be defined as follows.

$$\emptyset(T_R^{C'}) = \sum_{i=0}^{n} |V_{Bone\_C}(0, T_R^{C'} P'_{Ri})| \quad \langle\text{Equation 5}\rangle$$

Herein, $\emptyset(T_R^{C'})$ represents the distance between the coordinates of the new measured point and the surface of bone that is on the coordinate system C, $T_R^{C'}$ represents the new transformation matrix showing the relationship between the coordinate system R and the coordinate system C after the bone has been moved. $P'_{Ri}$ represents the position of new measured point on the coordinate system R, including the cut surface.

$P'_{Ri}$ can be classified into $P_{Bone\_Ri}'$ which are points on the surface of the original bone, and $P_{Cut\_Ri}'$ which are points on the cut surface. In this case, a difference between the original transformation matrix and the new transformation matrix represents the quantity of movement of bone.

In case that a difference between an average of distance from the surface of bone relating to the measured points on the surface of the original bone to the measured points, $$\frac{1}{n_1}\sum_{i=0}^{n_\pm} |V_{Bone\_C}(l, T_R^{C'} P'_{Bone\_Ri})|,$$

and an average of distance from the surface of bone relating to the measured points on the cut surface to the measured points, $$\frac{1}{n_2}\sum_{i=0}^{n_2} |V_{Bone\_C}(l, T_R^{C'} P'_{Cut\_Ri})|,$$

is bigger than a base value, it means that the result of the first registration, that is, the original transformation matrix is not correct.

The registration method according to the one embodiment of the present invention, which has been described above, is calculated based on the calculation of the cut volume and the registration result that found the shape of the cut bone for the first time. When the transformation matrix between two coordinate systems varies in real time, this method has difficulty in using practicably. However, in real surgery room, a bone is generally fixed, and during cutting operations, the measurement of position of the bone is performed for rechecking the position of bone or when the bone has been moved by momentary impacts. Thus, the difficulty of the registration method is not a big problem.

In addition, in case that the transformation matrix between two coordinate systems varies in real time, according to the registration method described above, the equations defined above are expanded to include the real-time variation of the transformation matrix. For example, the integral calculation in the equation 2, 3 will be defined in respect to time t, not to a level of progression of cut path L.

In robotic surgery cutting bones, because the shape of bone is not a neat geometric shape, after measuring the shape of bone in advance (by CT image, etc.) and measuring enough points of the surface of bone, the current position of bone is found by matching with the pre-recorded shape of bone. However, because a bone cannot be fixed tightly like in machine tools, while processing a bone according to pre-programmed processing sequences, when trying to re-find the position of bone due to movements of bone during surgery, it is difficult to re-find the position of bone with the same method. Because the bone has been changed into a shape that is quite different from the pre-recorded shape of bone due to the processing.

Therefore, according to the present invention, as explained above, the position of bone can be found again, using progression percentages of processing (0~100%) in cutting surgery, which is expressed as L in FIG. 5, and a shape of bone being processed that is predicted by the pre-recorded shape of bone based on the current progression percentages of processing, and the re-measured points on the surface of bone.

Figure 7:
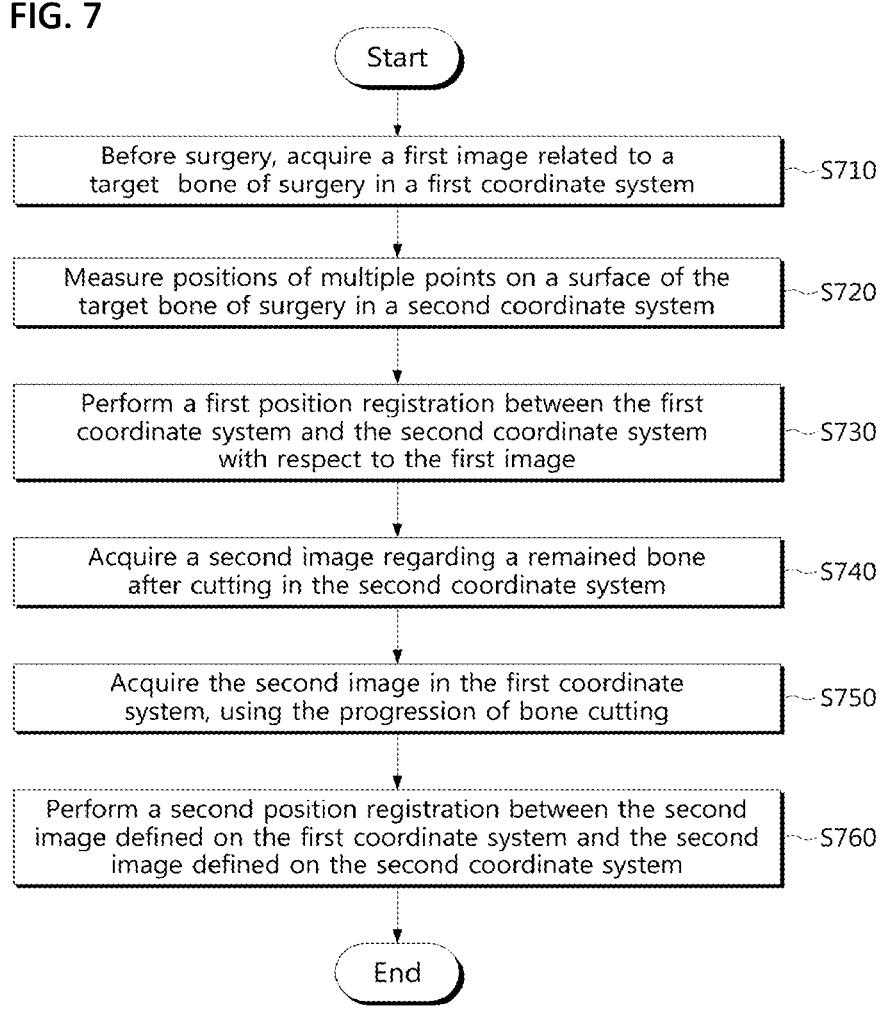
FIG. 7 is a flowchart that depicts the method for detecting positions of tissues according to the present invention.

FIG. 7 is a flowchart that depicts the method for detecting positions of tissues according to the present invention.

In explanation about an embodiment hereinafter, although it can be understood that each step of the method for detecting positions of tissues according to the present invention is performed in corresponding elements of the apparatus for detecting positions of tissues, which was explained through FIG. 1, the each step of the method should be limited as function itself, which defines the each step. In other words, the performer of each step is not limited by the names of elements that are given as examples of performer of each step.

According to the method for detecting positions of tissues, in step S710, before surgery, acquire a first image related to a target bone of surgery in a first coordinate system. The first coordinate system is a coordinate system on which an image of the target bone of surgery that is examined in advance before surgery is defined. The first coordinate system has been expressed as the coordinate system C in the preceding embodiments.

After that, in step S720, in real surgery room, measure positions of multiple points on a surface of the target bone of surgery in a second coordinate system. The second coordinate system is a coordinate system regarding a real bone existing in surgery room. The second coordinate system has been expressed as the coordinate system R in the preceding embodiments.

In step S730, after obtaining positions with respect to the first image on the first and the second coordinate system, a first position registration between the first and the second coordinate system is performed. In other words, the first position registration is performed by calculating a first transformation matrix between multiple points on the surface of bone of the first image, which are defined on the first coordinate system, and multiple points on the surface of bone of the first image, which are defined on the second coordinate system.

After that, in step S740, as the bone cutting is performed according to the progression of surgery, in the second coordinate system, acquire a second image, which is an image regarding a remained bone after cutting, applying a shape of the bone changed from the first image according to the progression of bone cutting. In this case, the shape of the remained bone after cutting includes unique shapes used in performing the position registration. The unique shapes are staircase shapes, groove shapes, fluted shapes, etc. Such unique shapes are used in calculating a transformation matrix, thereby greatly reducing computations.

As the second image has been required in the second coordinate system, in step S750, acquire the second image in the first coordinate system, using the progression of bone cutting. Specifically, subtract a transformed volume of bone, which is a cut volume of bone so far that is transformed into the first coordinate system, from a defined volume of bone that is defined by stored image information of the first coordinate system, using the first transformation matrix. As a result, the second image defined on the first coordinate system can be derived.

By the aforementioned procedures, the second image has been defined on the first and second coordinate system. After that, in step S760, perform a second position registration between the second image defined on the first coordinate system and the second image defined on the second coordinate system. That is, the second position registration is performed by calculating a second transformation matrix between first coordinates and second coordinates in respect with the second image. In this case, the second transformation matrix can be calculated by using multiple points on the surface of bone of the second image defined on the first coordinate system and multiple points on the surface of bone of the second image defined on the second coordinate system.

In a situation that the bone cutting is done using a surgical robot controlled by a computer, when re-searching or rechecking the position of bones being cut, the present invention that has been described above with the embodiments uses shapes of bones being cut, which are calculated according to the present invention. Therefore, it is possible to avoid damages of tissues or extra surgeries caused by attaching extra markers to bones, and to protect bones and tissues of a patient.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method for detecting positions of tissues, comprising:
   prior to surgery, acquiring a first image associated with a target bone of surgery in a first coordinate system;
   measuring position values of multiple points on a surface of the target bone of surgery in a second coordinate system, and performing a first position registration between the first coordinate system and the second coordinate system with respect to the first image;
   acquiring a second image regarding the remained bone after cutting in the second coordinate system by applying the shape of the bone changed according to the progression of bone cutting to the first image;
   acquiring the second image in the first coordinate system by using a level of the progression of bone cutting; and
   performing a second position registration with the second image defined on the first coordinate system and the second image defined on the second coordinate system;
   wherein the first coordinate system is a coordinate system on which an image of the target bone of surgery that is examined in advance before surgery is defined, and the second coordinate system is a coordinate system regarding the bone existing in surgery room.

2. The method according to claim 1, wherein performing the first position registration between the first coordinate system and the second coordinate system with respect to the first image comprises performing the first position registration by calculating a first transformation matrix between the first image defined on the first coordinate system and the first image defined on the second coordinate system.

3. The method according to claim 1, wherein performing the second position registration with the second image defined on the first coordinate system and the second image defined on the second coordinate system comprises performing the second position registration by calculating a second transformation matrix between the second image defined on the first coordinate system and the second image defined on the second coordinate system.

4. The method according to claim 1, wherein the shape of the remained bone after cutting includes a unique shape used in performing the position registration.

5. The method according to claim 2, wherein acquiring the second image in the first coordinate system by using the level of the progression of bone cutting comprises deriving the second image defined on the first coordinate system by using the first transformation matrix.

6. The method according to claim 2, wherein acquiring the second image in the first coordinate system by using the level of the progression of bone cutting comprises calculating a volume of the second image by subtracting a transformed volume of bone from a defined volume of bone,
   wherein the transformed volume of bone is a volume of cut bone that has been transformed into the first coordinate system, and the defined volume is a volume defined by information of the first image on the first coordinate system.

* * * * *